(12) United States Patent
Wu et al.

(10) Patent No.: US 8,268,634 B2
(45) Date of Patent: Sep. 18, 2012

(54) FLUID SAMPLE COLLECTING AND ANALYZING APPARATUS AND METHOD

(75) Inventors: John Wu, San Diego, CA (US);
Waiping Ng, San Diego, CA (US)

(73) Assignee: Ameditech, Inc., San Diego, CA (US)

( * ) Notice: Subject to any disclaimer, the term of this patent is extended or adjusted under 35 U.S.C. 154(b) by 190 days.

(21) Appl. No.: 12/745,239

(22) PCT Filed: Nov. 28, 2008

(86) PCT No.: PCT/US2008/013229
§ 371 (c)(1),
(2), (4) Date: May 27, 2010

(87) PCT Pub. No.: WO2009/073155
PCT Pub. Date: Jun. 11, 2009

(65) Prior Publication Data
US 2010/0311177 A1      Dec. 9, 2010

Related U.S. Application Data

(63) Continuation-in-part of application No. 11/998,610, filed on Nov. 29, 2007.

(51) Int. Cl.
*G01N 1/28* (2006.01)
(52) U.S. Cl. .......... 436/180; 436/177; 436/174
(58) Field of Classification Search ........... 422/406, 422/411, 410, 409, 405, 68.1, 500, 527, 570, 422/569; 436/174, 177, 178, 180, 176; 435/287.6, 435/287.7; 600/573, 575, 577
See application file for complete search history.

(56) References Cited

U.S. PATENT DOCUMENTS
2007/0208274 A1 *  9/2007 Ostrowski et al. ............ 600/573

FOREIGN PATENT DOCUMENTS
EP        1338338 A1 *  8/2003

OTHER PUBLICATIONS

Jerome, Keith R. et al. "Quantitative Stability of DNA after Extended Storage of Clinical Specimens as Determined by Real-Time PCR." Journal of Clinical Microbiology (2002) 40 2609-2611.* Uhl, James R. et al. "Use of the Roche LightCycler Strep B Assay for Detection of Group B Streptococcus from Vaginal and Rectal Swabs." Journal of Clinical Microbiology (2005) 43 4046-4051.*

* cited by examiner

*Primary Examiner* — Yelena G Gakh
*Assistant Examiner* — Christopher A Hixson
(74) *Attorney, Agent, or Firm* — Charmasson, Buchaca & Leach, LLP

(57) ABSTRACT

A spongy swab (16) is mounted against the distal face (15) of a piston (14) at the end of a push-rod (12). Once humected with a sample fluid, the swab and piston assembly is inserted into a tubular body (30) like the plunger of a syringe. As the swab is pushed and squeezed against the distal end (20) of the body up to a trippable stop, part of the fluid is excreted into a chromatographic immunoassay testing device (21) through a first aperture (19) in a distal section of the body. The remainder of the sample is kept in a sealed chamber (7) between the piston and the end wall of the tubular body until it is excreted through a second aperture (23) for a secondary test by pushing the piston beyond the trippable stop. That preserves the sample within the spongy swab that has been used to collect it; thus preventing the adsorption of the analytes on the surfaces of the sealed chamber, and to provide a convenient and rapid way to extract the remainder of the specimen in a syringe-like manner.

14 Claims, 3 Drawing Sheets

FLUID SAMPLE COLLECTING AND ANALYZING APPARATUS AND METHOD

FIELD OF THE INVENTION

The present invention relates to devices and methods for collecting and analyzing body fluids for the presence of one or more analytes by immunoassay testing techniques. More specifically, the invention relates to devices for collecting, testing, temporarily storing and transporting saliva samples.

BACKGROUND

Testing for substance abuse has become standard procedure in a variety of settings such as employment, schools, sports, and law enforcement. The industry has so far provided a great variety of easy-to-use collecting and testing devices which can be utilized by technicians with limited training in the field for preliminary test purposes.

Due to the speed at which the devices of the prior art are used, the relative lack of sophistication of the technicians, and the less than propitious environment of the test, it has become desirable, if not mandatory, to preserve an aliquot of the sample fluid for further testing and validation under more controlled conditions to seek to confirm the results of the earlier preliminary test.

U.S. Patent Application Publication No. US2005/0202568 A1 Tung et al. dated Sep. 15, 2005, incorporated herein by this reference, discloses a sophisticated device which provides for the preservation of part of the fluid specimen in a sealed plastic reservoir for confirmatory testing at a later date. Such a sophisticated device can be costly to manufacture, requires more operator skill and time to use, and is more susceptible to manufacturing or use errors.

It is well known that small amounts of analytes, such as those associated with marijuana or other abused drugs, can be adsorbed over time on the surfaces of fluid specimen containers. Such adsorption reduces the concentration of analytes remaining in the specimen leading to inaccuracies in testing results associated with detection of those analytes. This problem can be exacerbated by containers used to transport specimens for confirmatory testing where the specimen remains in the container for longer periods and is subjected to agitation and temperature changes during transport. It is therefore desirable to preserve an aliquot of the fluid specimen in such a way as to minimize adsorption of target analytes on the aliquot container surfaces.

The invention results from an attempt to devise a simpler apparatus that reduces some of the above identified problems.

SUMMARY

The principal and secondary objects of the invention are to provide a simpler collection and test apparatus that preserves part of a fluid sample for later processing. These and other objects are achieved by an apparatus which preserves part of the fluid sample within the spongy swab that has been used to collect it.

In some embodiments there is provided a fluid sample collecting and testing device having a spongy cylindrical swab is axially mounted against the distal face of a piston actioned by a push rod. In some embodiments once humected with a sample fluid such as saliva, the swab-and-piston assembly is inserted into a tubular body like a plunger into a syringe. In some embodiments as the swab is pushed and partially squeezed against the distal end of the tubular body, and up to a trippable barrier, part of the fluid is excreted into a immunoassay device through a radial aperture in the distal section of the body. In some embodiments the remainder of the sample is kept in a sealed chamber between the piston and the closed distal end of the body until it is excreted through a second aperture until then sealed by a breakable barrier directly into another immunoassay testing device.

In some embodiments the apparatus comprises a plunger including a push rod, a piston attached to one extremity of the push rod, said piston having a distal face, and a spongy swab axially mounted on the distal face; a tubular body open at a first end, closed at an opposite second end, and being dimensioned to be intimately engaged by the piston; the body having at least one exit port proximate the second end; and a trippable barrier positioned to stop the piston distally from the second end; and wherein the swab is dimensioned to be partially squeezed between the distal face of the piston and the second end of the body when the distal face reaches its stopping location determined by the trippable barrier.

In some embodiments the apparatus further comprises an immunoassay testing device connected to the exit port. In some embodiments the exit port is radially positioned proximately distant from the stopping location of the piston. In some embodiments the body has a second exit port located distally from the stopping location, and further includes a breakable stopper closing the second exit. In some embodiments the apparatus also comprises a second immunoassay testing device detachably securable to the second exit port. In some embodiments the trippable barrier comprises at least one radial protrusion on the plunger positioned to contact the tubular body when the distal face of the piston reaches the stopping location. In some embodiments the protrusion is manually compressible or removeable. In some embodiments, the exit port is axially positioned in the second end of the body. In some embodiments the exit port is closed by a breakable seal. In some embodiments the trippable barrier is tripped by increased forced insertion of said plunger into the body. In some embodiments the piston may comprise a peripheral O-ring. In some embodiments the body has a circumferential inside groove having an hemispherical cross-section commensurate with the O-ring; whereby the engagement of the O-ring into the groove constitutes the trippable barrier. In some embodiments the exit port is radially located within the groove. In some embodiments a threaded coupling is provided between the exit port and the testing device.

In some embodiments essentially the collecting and testing apparatus comprises: a syringe-like plunger and tubular body assembly, the tubular body having a closed distal end; a spongy swab distally mounted on the plunger; a trippable barrier preventing the swab from being completely squeezed between the plunger and the distal end of the tubular body; and an analyte testing device connected to an exit port in a distal region of the tubular body.

In some embodiments there is provided a method for conducting a first preliminarily test on a fluid sample while preserving a portion of said sample for later testing, and dispensing said portion during said later testing, said method comprises: collecting said fluid sample upon a spongy swab distally mounted on a syringe-like plunger; extracting a first partial portion of said sample from said swab, thereby leaving a second partial portion of said sample on said swab; directing said first partial portion onto a fluid test device capable of detecting said analyte to obtain a preliminary detection; hermetically enclosing said swab in an openable chamber; forming an opening in said chamber; and, excreting said second partial portion through said opening. In some embodiments said extracting comprises: inserting said plunger a first distance into a tubular body assembly having a closed distal end;

preventing insertion of said plunger beyond said first distance using a trippable barrier; tripping said trippable barrier; further inserting said plunger beyond said first distance, thereby causing said excreting.

DESCRIPTION OF THE EXEMPLARY EMBODIMENTS

Figure 1:
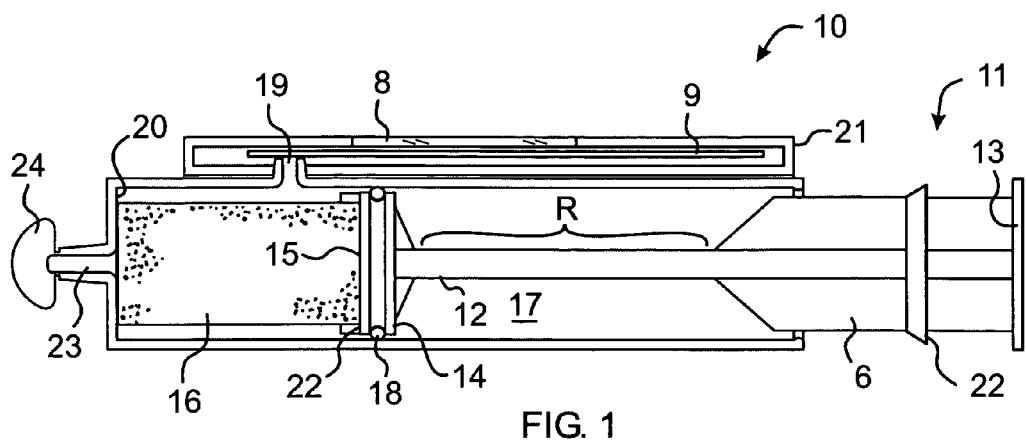
FIG. 1 is an illustrative cross-sectional view of a first embodiment of the collecting and testing apparatus according to the invention shown in a first fluid extracting mode.
Figure 2:
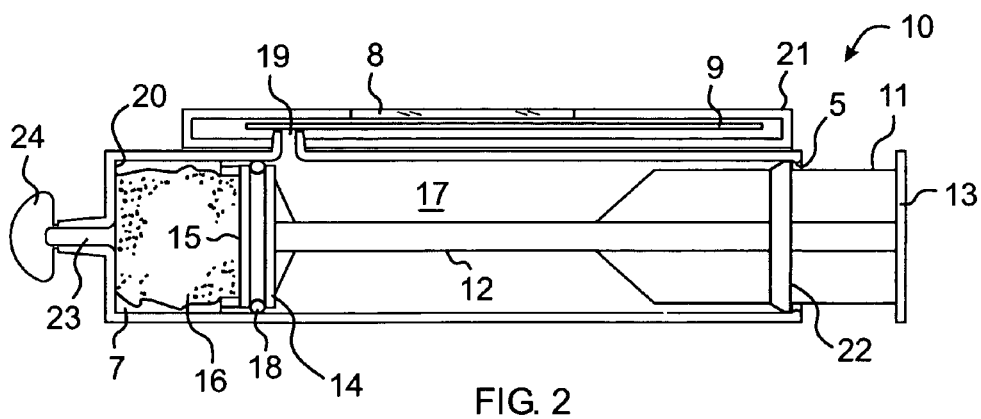
FIG. 2 is a similar view with the apparatus shown in a post first extraction mode.

Referring now to the drawing, there is shown in FIGS. 1 and 2, an apparatus 10 for collecting, testing, storing and transporting a fluid sample such as a saliva specimen. The apparatus comprises a plunger 11 including a push rod 12 having a thumb rest 13 at its proximal end and a piston 14 at the distal end of the rod. The piston has a distal face 15 against which is axially attached a cylindrical spongy swab 16. The plunger is first used to collect the fluid sample by contact with the swab.

The push rod 12 is shaped and dimensioned to have a medial lip-rest region R which allows a user to comfortably close her lips upon it while the swab remains in the user's mouth. The axial length of the lip-rest region is selected to accommodate the closed lips and teeth of a typical adult user. In such circumstances it has been found that the length is preferably between about 2.54 centimeters (1.0 inch) and 5.08 centimeters (2.0 inches), more preferably between about 3.175 centimeters (1.25 inches) and 4.445 centimeters (1.75 inches), and most preferably about 3.81 centimeters (1.5 inches).

The plunger is then inserted and translated axially in a tubular body 17 which is dimensioned to be intimately engaged by the piston 14. An O-ring 18 peripherally mounted on the wall of the piston provides an hermetical seal between the inside of the tubular body and the piston. A radial exit port 19 is located proximately distant from the end wall 20 of the tubular body, that is ahead of the end wall. A centering element 6 is located distally from the thumb rest 13 to helps maintain a coaxial relationship between the plunger 11 and body 17 during the forced insertion of the plunger. In order to accommodate these forces, the location of the centering element is selected to cause it to engage the tubular body before compression of the swab begins. A second exit port 23 axially practiced in the end wall 20 is sealed by a breakable stopper 24.

As the plunger is pushed into the tubular body, the spongy swab 16 is squeezed between the distal face of the piston 15 and the end wall 20. The part of the sample fluid within the swab is excreted through the exit port 19 and into a chromatographic immunoassay test device 21 secured to and in fluid communication with the exit port 19. The test device 21 is adapted to carry one or more chromatographic testing strips 9 viewable through an exposed window 8 according to techniques well-known in the bio-medical arts.

As shown in FIG. 2, when the penetration of the plunger proceeds beyond where the piston O-ring 18 has passed the exit port 19, the swab containing the aliquot of fluid specimen becomes hermetically enclosed in a chamber 7 formed in the tubular body between the end wall and piston. The small amount of remaining gas in the chamber compresses but the fluid does not, effectively preventing further penetration of plunger beyond a stopping position illustrated in FIG. 2, at a point where the swab 16 is not completely squeezed and still contains an aliquot of fluid specimen. The radial exit port 19 is proximally distant, i.e. just ahead from the point where the distal face 15 of the piston is temporarily stopped. This arrangement acts as a barrier to further penetration due to the pressure increase in the chamber when further penetration is attempted.

A compressible barrier 22 in the form of a rubber radial projection such as a retaining ring glued to the plunger passes over the lip 5 at the proximal end of the tubular body and indicates to the operator that penetration has proceeded to an adequate degree. The ring is flared outwardly toward the proximal end so as to discourage extraction of the plunger from the body. In addition the enclosure creates what amounts to a vacuum seal which can help to prevent the extraction of the plunger. In this way preservation of the aliquot is enhanced over other designs in which the reverse motion of the plunger is allowed.

The swab is biased toward its uncompressed state. In this way the compressed swab tends to substantially fill the chamber 7 further discouraging fluid circulation during transport. That aliquot is preserved within the swab which prevents circulation of the aliquot against the container surfaces thereby discouraging loss of analytes due to adsorption on the container surfaces. The swab material also acts to thermally insulate the preserved fluid against temperature changes thereby further decreasing analyte loss through adsorption.

The barrier is trippable, that is, it may be overcome by removal of the stopper 24 and forced further penetration of the plunger into the tubular body through application of additional pressure against the thumb rest 13. The remaining fluid specimen can thus be extracted at a later date to conduct a confirming test by breaking the stopper 24, and forcefully pushing the piston as far as is necessary to fully compress the swab 16. It should be understood that the dimensions of the tubular body and location of the radial exit port are selected so that fluid pressure in the chamber can substantially prevent further compression of the swab until the stopper is removed, and thereby act as a trippable barrier.

Because of the number of functions which are provided by the plunger, care must be taken in determining the relative sizes and shapes of the component structures. For example, the push rod should have low bulk to accommodate comfortable closure of the users lips upon it while still providing enough material to provide a strength to withstand the forces of insertion into the tubular body and forced compression of the swab.

Figure 3:
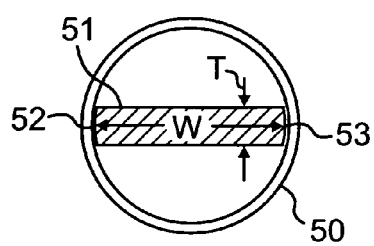
FIG. 3 is an illustrative cross-sectional end view of an alternate embodiment having a widened and flattened push-rod.

Alternately, the push rod can be formed to have an elongated, flattened shape to enhance its strength while still providing adequate clearance and comfort to the user. As shown in FIG. 3, the width W of the push rod 50 is flattened and widened to be commensurate with the inner diameter of the tubular body 51. Further, the lateral edges 52,53 of the rod can be curved to intimately bear against the curved inner surface of the tubular body. The thickness T is minimized while still affording adequate resistance to bending and column strength to the push rod. This shape allows for the users lips to be comfortably closed thereon in the medial lip-rest region and act as a centering element, if necessary, along the entire length of the push rod.

Figure 4:
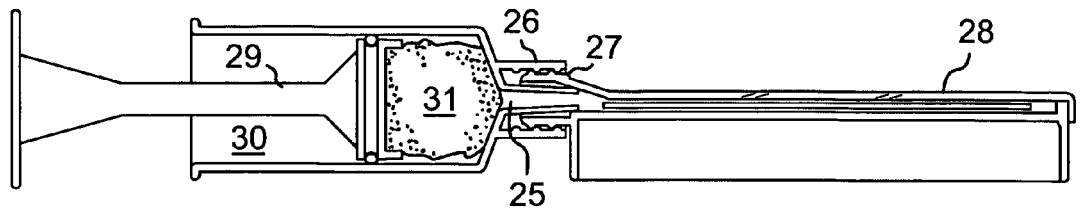
FIG. 4 is an illustrative cross-sectional view of an alternate embodiment of the testing apparatus having an end-mountable immunoassay device.

Referring now to FIG. 4, there is shown a second embodiment of the invention in which no radial exit port is provided as in the first embodiment. Instead, an axial exit port 25 in the end wall has a threaded coupling 26 that mates with the inlet coupling 27 of a detachable immunoassay device 28.

As in the first embodiment, the progress of the plunger 29 within the tubular body 30 is first stopped at a given distance from the end wall either by a trippable barrier (as shown in FIGS. 6-11) or purposefully by the operator. Accordingly, a first test device may be used to receive and preliminarily analyze a portion of the specimen fluid extracted by the first partial compression of the swab 31, and a second test device may be used later on to analyze the remainder of the sample fluid excreted by the complete squeezing of the swab 31. It should be understood that the immunoassay device 28 can be detached at the threaded coupling and replaced with a threaded cap, such as the cap 34 shown in FIG. 5, to hermetically enclosed the aliquot and allow its transport to a different location for excretion.

Figure 5:
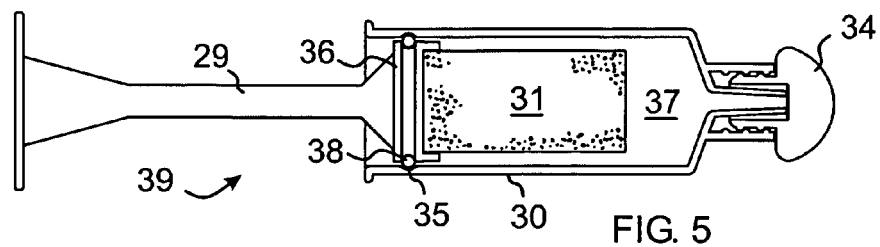
FIG. 5 is an illustrative cross-sectional view of an alternate embodiment of the testing apparatus for use as a specimen collection, transport and dispensing syringe.

Referring now to FIG. 5, it should be noted that the plunger 29 carrying the swab 31 and the tubular body 30 along with a stopper 34 can be provided separately without any immunoassay device to allow for collection, storage and transport of the fluid specimen to a lab where testing occur. In this way, the plunger and swab are used to collect a specimen. The plunger 29 is then inserted into the body 30 having the stopper 34 already in place. The stopper can be of the threaded cap type, as shown, or of the breakable type shown in the embodiment of FIGS. 1 and 2. The plunger engages the body until the O-ring 38 engages a circumferential groove 35 set into the inside wall of the body. The groove has a hemispherical cross-section commensurate with the cross-section of the O-ring 38 that surrounds the piston 36. This encloses the specimen carried on the swab in a hermetically sealed chamber 37 formed between the plunger and the body. The engagement of the O-ring into the groove, coupled with the increase in pressure of the chamber acts as a trippable barrier to the further insertion of the plunger. The combined structure 39 of the plunger and body can then be transported to a lab or other location where the stopper can be removed and an immunoassay device of the type shown in FIG. 4 attached and testing carried out.

It is important to note that with the stopper removed, the combined structure can be conveniently used by a lab operator as a syringe to dispense the specimen fluid into a number of various devices.

Figure 6:
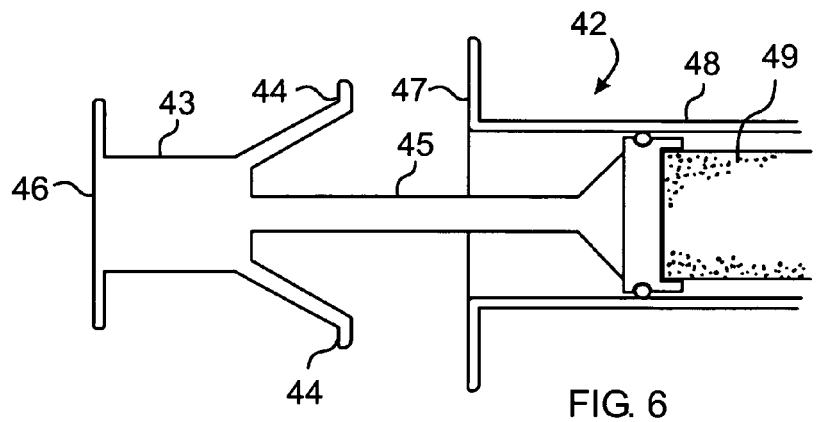
FIGS. 6 and 7 illustrate a second type of trippable barrier.
Figure 7:
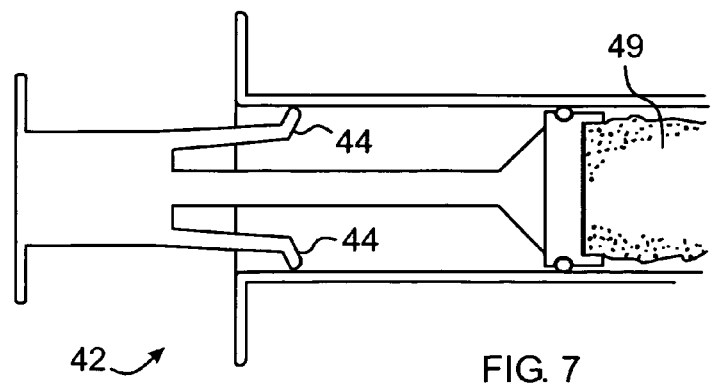

A second type of trippable barrier 42 is illustrated in FIGS. 6 and 7. The plunger 43 is provided with a series of peripheral prongs 44 which skirt the push rod 45 at a short distance from the thumb rest 46. The prongs flexibly flare out to form an impediment to the progression of the plunger when they come in contact with the rim 47 of the tubular body 48. The prongs can be deactivated by being compressed between thumb and index finger so that they will penetrate the tubular body as shown in FIG. 6 allowing the plunger to further push against the swab 49.

Figure 8:
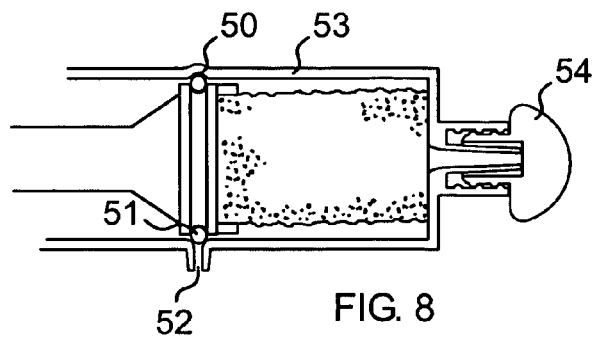
FIG. 8 illustrates a third type of trippable barrier.

A third type of trippable barrier is illustrated in FIG. 8. A circumferential groove 50 is provided in the inside wall of the tubular body 53. The groove has a hemispherical cross-section commensurate with the cross-section of the O-ring 51 that surrounds the piston. The radial exit port 52 corresponding to the exit port 19 of FIG. 1 is located within the groove. When the O-ring, which is normally slightly compressed by the walls of the tubular enclosure, reaches the groove 50 it expands into it. This expansion stops the progress of the piston at the location corresponding to the point necessary to squeeze out a part of the sample fluid. In addition, the O-ring provides a positive closure of the radial exit port 52. The remainder of the fluid in the swab is now preserved in a sealed chamber between the piston and the end wall of the tubular enclosure. By removing the end stopper 54 and applying additional or increased pressure on the plunger, the barrier can be overcome in order to extract the remainder of the fluid specimen through the exit port at the end of the body.

Figure 9:
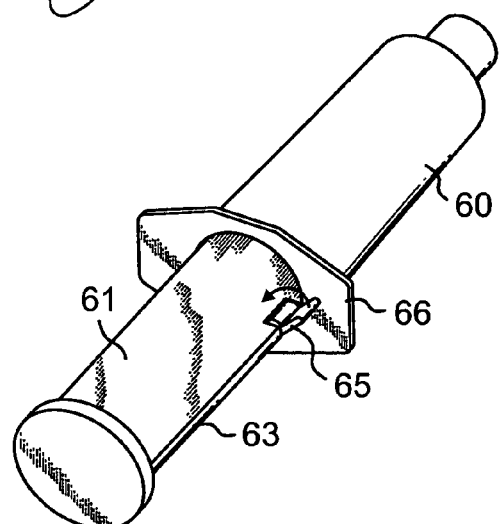
FIG. 9 illustrates a fourth type of trippable barrier.

A fourth type of trippable barrier is shown in FIG. 9. A rigid flap 65 is hingedly mounted to the lateral edge 63 of a push-rod 61. In its open position (shown) the flap acts as a radial prominence which contacts the rim 66 of the tubular body 60 to prevent further penetration. The flap is deactivated by folding it inward against the rod allowing penetration to proceed.

Figure 10:
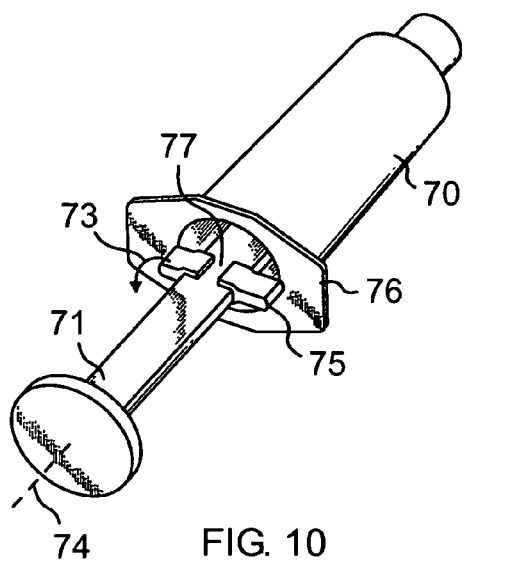
FIGS. 10 and 11 illustrate a fifth type of trippable barrier.
Figure 11:
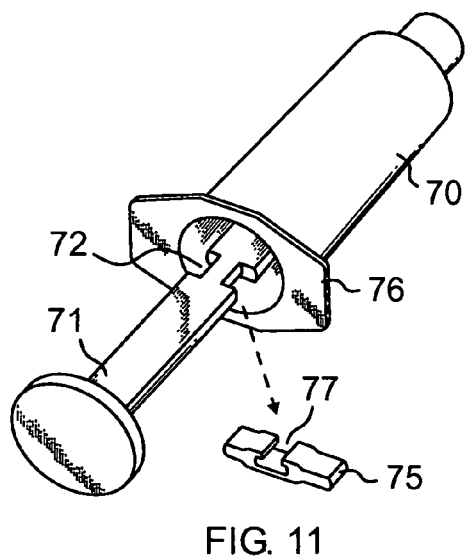

A fifth type of trippable barrier is shown in FIGS. 10-11. A detachable winglet 75 is mounted within a cradle 72 formed by two indentations set into the opposite lateral edges of a medial section of a push-rod 71 having a flattened, oblong cross-section. In its mounted position (shown in FIG. 10) the winglet 75 acts as a radial prominence which contacts the rim 76 of the tubular body 70 to prevent further penetration. The winglet is detached by rotating it angularly 73 with respect to the insertion axis 74 of the plunger so that a notch 77 on the upper medial edge of the winglet aligns with a narrower dimension of the cradle of the flattened push-rod 71. Alternately, the winglet can be made from a slightly resilient material which allows the notch to be widened to facilitate removal of the winglet from the push-rod.

While the preferred embodiments of the invention have been described, modifications can be made and other embodiments may be devised without departing from the spirit of the invention and the scope of the appended claims.

What is claimed is:

1. A method for conducting a first preliminary test on a fluid sample while preserving a portion of said sample for later testing, and dispensing said portion during said later testing, said method comprises:
   collecting said fluid sample upon a spongy swab distally mounted on a syringe-like plunger;
   extracting a first partial portion of said sample from said swab, thereby leaving a second partial portion of said sample on said swab;
   directing said first partial portion onto a fluid test device capable of detecting an analyte to obtain a preliminary detection;
   hermetically enclosing said swab in an openable chamber;
   forming an opening in said chamber; and,
   excreting said second partial portion through said opening;
   wherein said extracting comprises:
      inserting said plunger a first distance into a tubular body assembly having a closed distal end;
      preventing insertion of said plunger beyond said first distance using a trippable barrier;
      tripping said trippable barrier; and,
   wherein said method further comprises:
      further inserting said plunger beyond said first distance, thereby causing said excreting.

2. The method of claim 1, wherein said inserting comprises:
  intimately engaging a piston included at the distal end of the plunger into the tubular body.

3. The method of claim 1, wherein said hermitically enclosing comprises hermetically sealing the piston to the tubular body.

4. The method of claim 1, wherein said method further comprises:
  including a push-rod on said plunger having a medial lip-rest region enclosable by a user's closed lips and having sufficient bending resistance and column strength to withstand the forces of said inserting and said further inserting.

5. The method of claim 1, wherein said inserting and said further inserting are coaxial.

6. The method of claim 1, which further comprises centering the plunger and tubular body using a centering element.

7. The method of claim 6, wherein said centering occurs prior to and during said extracting.

8. The method of claim 1, wherein said excreting comprises squeezing the swab between the piston and the distal end of the tubular body.

9. The method of claim 8, wherein said squeezing comprises compressing a small amount of remaining gas in the openable chamber.

10. The method of claim 1, wherein said hermetically enclosing comprises substantially filling the chamber with the swab.

11. The method of claim 1, wherein said tripping comprises:
  passing a retaining ring on the plunger over a lip on the tubular body.

12. The method of claim 1, which further comprises detaching an immunoassay device from said tubular body.

13. The method of claim 1, wherein said tripping comprises: inwardly folding a radially prominent flap mounted on the plunger away from contacting the tubular body.

14. The method of claim 1, wherein said tripping comprises: detaching a radially prominent winglet mounted on the plunger from contacting the tubular body.

* * * * *